US012806424B2

(12) United States Patent
Jung et al.

(10) Patent No.: US 12,806,424 B2
(45) Date of Patent: Nov. 24, 2026

(54) STRETCHABLE ELECTRODE ASSEMBLY

(71) Applicants: Heraeus Deutschland Gmbh & Co. KG, Hanau (DE); Heraeus Medical Components LLC, St. Paul, MN (US)

(72) Inventors: Markus Jung, Hanau (DE); Katharina Musiol, Hanau (DE); Oliver Keitel, Hanau (DE); Steven E. Scott, Fridley, MN (US)

(73) Assignees: Heraeus Medevio GmbH & Co. KG, Hanau (DE); Heraeus Medical Components LLC, St. Paul, MN (US)

( * ) Notice: Subject to any disclaimer, the term of this patent is extended or adjusted under 35 U.S.C. 154(b) by 302 days.

(21) Appl. No.: 17/083,869

(22) Filed: Oct. 29, 2020

(65) Prior Publication Data

US 2022/0134113 A1 May 5, 2022

(51) Int. Cl.

| | |
|---|---|
| ***A61N 1/375*** | (2006.01) |
| ***A61B 5/263*** | (2021.01) |
| ***A61N 1/05*** | (2006.01) |
| ***H05K 1/02*** | (2006.01) |
| *A61N 1/36* | (2006.01) |

(52) U.S. Cl.

CPC .............. *A61N 1/375* (2013.01); *A61B 5/263* (2021.01); *A61N 1/05* (2013.01); *H05K 1/0277* (2013.01); *A61N 1/36* (2013.01); *H05K 1/0283* (2013.01)

(58) Field of Classification Search

CPC . A61N 1/375; A61N 1/05; A61N 1/36; A61N 1/0553; A61N 1/0492; A61N 1/0484; A61N 1/0476; A61B 5/263; H05K 1/0277; H05K 1/0283

See application file for complete search history.

(56) References Cited

U.S. PATENT DOCUMENTS 3,834,373 A * 9/1974 Sato ........................ A61B 5/257 252/514
4,690,148 A * 9/1987 Hess ...................... A61B 5/282 600/374
4,840,186 A * 6/1989 Lekholm ................ A61N 1/056 607/116

(Continued)

FOREIGN PATENT DOCUMENTS

DE 10 2019 218 477 6/2021

*Primary Examiner* — Pamela M. Bays
(74) *Attorney, Agent, or Firm* — Dicke, Billig & Czaja, PLLC

(57) ABSTRACT

One aspect relates to a stretchable electrode assembly for a stimulation, modulation or sensing implant comprising an electrical conductor segment comprising at least one electrical conductor which is an electrically insulated wire or cable, and at least one electrode which is adjacent to the electrical conductor segment, wherein the electrical conductor segment is at least partially embedded in a biocompatible substrate and the electrical insulation of the at least one electrical conductor comprises one or more opening(s) suitable for mechanically and electrically connecting the at least one electrode to the at least one electrical conductor of the electrical conductor segment. One aspect also relates to a stimulation, modulation or sensing implant comprising the stretchable electrode assembly as well as a method for preparing such a stretchable electrode assembly.

10 Claims, 6 Drawing Sheets

(56) References Cited

U.S. PATENT DOCUMENTS

| | | | | |
|---|---|---|---|---|
| 2007/0027514 | A1* | 2/2007 | Gerber | A61N 1/05 607/116 |
| 2007/0123963 | A1* | 5/2007 | Krulevitch | A61N 1/0551 607/115 |
| 2008/0046051 | A1* | 2/2008 | Skubitz | A61N 1/3605 607/116 |
| 2011/0034912 | A1* | 2/2011 | de Graff | H01L 27/14632 606/41 |
| 2013/0303873 | A1* | 11/2013 | Voros | H05K 1/0283 604/20 |
| 2014/0107455 | A1 | 4/2014 | Regnier et al. | |
| 2021/0162206 | A1 | 6/2021 | Jung et al. | |

* cited by examiner

STRETCHABLE ELECTRODE ASSEMBLY

TECHNICAL FIELD

One aspect relates to a stretchable electrode assembly for a stimulation, modulation or sensing implant comprising an electrical conductor segment comprising at least one electrical conductor which is an electrically insulated wire or cable, and at least one electrode which is adjacent to the electrical conductor segment, wherein the electrical conductor segment is at least partially embedded in a biocompatible substrate and the electrical insulation of the at least one electrical conductor comprises one or more opening(s) suitable for mechanically and electrically connecting the at least one electrode to the at least one electrical conductor of the electrical conductor segment. One aspect also relates to a stimulation, modulation or sensing implant comprising the stretchable electrode assembly as well as a method for preparing such a stretchable electrode assembly.

BACKGROUND

Implants for stimulation, modulation or sensing are used in a great variety of applications. For example, such implants are used for cardiac pacemakers correcting heartbeat abnormalities, or for neuromodulation therapies suitable for reestablishing neural balance. More precisely, implants for neuromodulation therapies are typically used to enhance or suppress activity of the nervous system for the treatment of a disease, whereby the implant delivers electrical stimulation to reversibly modify brain and nerve cell activity. Common neuromodulation devices are used for spinal cord stimulation to treat chronic neuropathic pain; deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; vagus nerve stimulation for epilepsy, obesity or depression; carotid artery stimulation for hypertension, and spinal cord stimulation for ischemic disorders such as angina and peripheral vascular disease. Such implants typically contain electronics connected to leads that deliver electrical pulses to electrodes interfaced with nerves or nerve bundles via an electrode assembly.

Conventional electrode assemblies may be made out of bulk silicone, which is biocompatible and soft enough to mitigate most tissue damage during normal motion of the assembly against its implanted surroundings. Most often such implants are prepared by semi-conductor manufacturing technologies like lithography, which method however is quite restricting for the form and shape of the final implant. Other methods include thin film based technologies, which however, are quite complex. Furthermore, implants prepared by thin film based technologies are typically not suitable for prolonged use because the stiffness of the material is in general too high for the tissue surrounding the implant resulting in blood clots, and other tissue damages. In view of the above, there is still a need for an electrode assembly suitable for a stimulation, modulation or sensing implant, wherein the electrode assembly is soft and stretchable. Furthermore, it is desired that the electrode assembly is flexible in design and adoptable for many application. It is additionally desired that the electrode assembly is easy to manufacture without the necessity of semi-conductor technologies and, moreover, is easy to implement in existing manufacturing infrastructures.

Therefore, the present embodiments are directed to the provision of an improved, or at least alternative, soft and stretchable electrode assembly suitable for a stimulation, modulation or sensing implant.

SUMMARY

The foregoing and other objects are solved by the subject-matter as defined in the independent claims. Advantageous embodiments of the present invention are defined in the corresponding subclaims.

One embodiment provides a stretchable electrode assembly for a stimulation, modulation or sensing implant comprising an electrical conductor segment comprising at least one electrical conductor which is an electrically insulated wire or cable, and at least one electrode which is adjacent to the electrical conductor segment, wherein the electrical conductor segment is at least partially embedded in a biocompatible substrate and the electrical insulation of the at least one electrical conductor comprises one or more opening(s) suitable for mechanically and electrically connecting the at least one electrode to the at least one electrical conductor of the electrical conductor segment.

The inventors surprisingly found out that the electrode assembly is suitable for a stimulation, modulation or sensing implant, wherein the electrode assembly is soft and stretchable. Furthermore, the electrode assembly is flexible in design and adoptable for many application and, moreover, it is easy to manufacture without the necessity of semi-conductor technologies and is easy to implement in existing manufacturing infrastructures.

According to one embodiment, the at least one electrical conductor and/or at least one electrode comprise(s) one or more of the metals Pt, Ir, Ta, Pd, Ti, Fe, Au, Mo, Nb, W, Ni, Ti, Ag, Cu, or a mixture and/or alloy thereof and/or the at least one electrical conductor and/or the at least one electrode is/are a multilayered material system(s).

According to one embodiment, the electrical insulation of the at least one electrical conductor comprises an insulating plastic material, in one embodiment an insulating plastic material selected from the group comprising polyethylene, polyurethane, polyimide, polyamide, PEEK, and fluorinated plastic materials such as ETFE, PTFE, PFA, PVDF, FEP or FPO, and mixtures thereof.

According to one embodiment, the biocompatible substrate is selected from the group comprising polyurethane, thermoplastic polyurethane (TPU), silicone, polyimide, phenyltrimethoxysilane (PTMS), polymethylmethacrylate (PMMA), parylene, polyetheretherketone (PEEK), liquid-crystal polymer (LCP), kapton and mixtures thereof. According to one embodiment, the at least one electrical conductor of the electrical conductor segment is a bundle of electrical conductors and each electrical conductor is electrically insulated.

According to one embodiment, the electrical conductor segment and the biocompatible substrate are welded joint.

According to one embodiment, the at least one electrode is/are mechanically and electrically connected to the at least one electrical conductor by welding, adhesives, brazing, soldering, conductive polymer or metal bridges, and/or dimples which are pressed through the opening of the electrical insulation of the at least one electrical conductor. According to one embodiment, the stretchable electrode assembly has a thickness ranging from 0.4 to 1.5 mm and/or is soft.

According to another aspect, a stimulation, modulation or sensing implant comprising the stretchable electrode assembly as defined herein is provided.

According to one embodiment, the stimulation, modulation or sensing implant is a neuro modulation device, spinal cord stimulator, neuro stimulator device, cortical mapping device, heart muscle stimulator device or electrophysiology device.

According to a further aspect, a method for preparing a stretchable electrode assembly as defined herein is provided, the method comprising the steps of a) providing at least one electrical conductor which is an electrically insulated wire or cable,
b) providing at least one electrode,
c) providing a biocompatible substrate,
d) adding one or more opening(s) into the electrical insulation of the at least one electrical conductor suitable for mechanically and electrically connecting the at least one electrode to the at least one electrical conductor,
e) assembling the at least one electrode to the one or more opening(s) in the electrical insulation of the at least one electrical conductor, whereby a mechanical and electrical connection between them is formed in a firmly-bonded and/or force-locked manner, and
f) covering the at least one electrical conductor before or after step d) and/or before or after step e) with the biocompatible substrate such that the electrical conductor is at least partially embedded in the biocompatible substrate.

According to one embodiment, the method comprises the steps of:

a) arranging the at least one electrical conductor in one or more pre-shaped groove(s) of fixture to form an electrical conductor segment,
b) covering the electrical conductor segment with a biocompatible substrate such that the electrical conductor segment is partially embedded in the biocompatible substrate,
c) removing the electrical conductor segment which is partially embedded in the biocompatible substrate from the pre-shaped groove(s) of fixture,
d) adding one or more opening(s) into the electrical insulation of the at least one electrical conductor suitable for mechanically and electrically connecting at least one electrode to the at least one electrical conductor, and
e) assembling at least one electrode to the one or more opening(s) in the electrical insulation of the at least one electrical conductor, whereby a mechanical and electrical connection between them is formed in a firmly-bonded and/or force-locked manner.

According to one embodiment, the one or more pre-shaped groove(s) of fixture provide the final shape of the stretchable electrode assembly.

According to one embodiment, the method comprises a further step of micro-structuring or coating the at least one electrode of the stretchable electrode assembly.

According to one embodiment, the method comprises a further step of attaching one or more anchors for spacer.

It should be understood that for the purposes of the present embodiments, the following terms have the following meanings:

Where an indefinite or definite article is used when referring to a singular noun, e.g., "a", "an" or "the", this includes a plural of that noun unless anything else is specifically stated. Where the term "comprising" is used in the present description and claims, it does not exclude other elements. For the purposes of the present embodiments, the terms "essentially consisting of" and "consisting of" are considered to be a preferred embodiment of the term "comprising". If hereinafter a group is defined to comprise at least a certain number of embodiments, this is also to be understood to disclose a group, which in one embodiment essentially consists of only of these embodiments, or in one embodiment consists of only of these embodiments. Terms like "obtainable" or "definable" and "obtained" or "defined" are used interchangeably. This, for example, means that, unless the context clearly dictates otherwise, the term "obtained" does not mean to indicate that, for example, an embodiment must be obtained by, for example, the sequence of steps following the term "obtained" though such a limited understanding is always included by the terms "obtained" or "defined" as a preferred embodiment.

Whenever the terms "including" or "having" are used, these terms are meant to be equivalent to "comprising" as defined hereinabove.

BRIEF DESCRIPTION OF THE DRAWINGS

The following schematic drawings show aspects of the invention for improving the understanding of the invention in connection with some exemplary illustrations, wherein.

DETAILED DESCRIPTION

Figure 1:
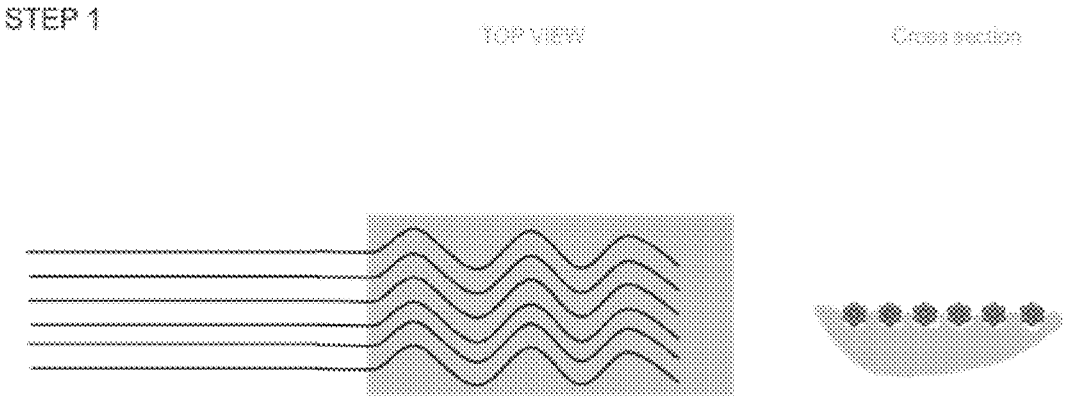
FIG. 1 shows a schematical top and sectional illustration of step 1 of a method for preparing the stretchable electrode assembly.

One aspect of the present embodiments refers to a stretchable electrode assembly for a stimulation, modulation or sensing implant comprising an electrical conductor segment comprising at least one electrical conductor which is an electrically insulated wire or cable, and at least one electrode which is adjacent to the electrical conductor segment, wherein the electrical conductor segment is at least partially embedded in a biocompatible substrate and the electrical insulation of the at least one electrical conductor comprises one or more opening(s) suitable for mechanically and electrically connecting the at least one electrode to the at least one electrical conductor of the electrical conductor segment.

The stretchable electrode assembly comprising an electrical conductor segment comprising at least one electrical conductor which is an electrically insulated wire or cable. In one embodiment, the at least one electrical conductor is an electrically insulated wire.

It is to be noted that a "wire" in the meaning of the present embodiments refers to a single wire. The term "cable" refers to a bundle of at least two wires, in one embodiment a (regularly) twisted bundle of at least two wires. For example, the cable comprises two to ten wires, in one embodiment three to nine wires. It is appreciated that each electrical conductor in form of either a wire or a cable is separately insulated by an insulating plastic material. That is to say, if the at least one electrical conductor is a cable, each wire in the cable is electrically insulated and the bundle of wires is again electrically insulated by an insulating plastic material. The term "at least one" electrical conductor in the meaning of the present embodiments means that the electrical conductor segment comprises, in one embodiment consists of, one or more electrical conductor(s).

In one embodiment, the electrical conductor segment comprises, in one embodiment consists of, one electrical conductor. Alternatively, the electrical conductor segment comprises, in one embodiment consists of, two or more electrical conductors. For example, the electrical conductor segment comprises, in one embodiment consists of, two to eight electrical conductors. In one embodiment, the electrically insulated wire or cable has a thickness ranging from 5 to 200 μm, in one embodiment ranging from 10 to 120 μm. In one embodiment, the electrically insulated wire or cable has an intrinsic flexibility such that it can be arranged into a desired form, into the one or more pre-shaped groove(s) of fixture to form the electrical conductor segment. It is to be noted that the at least one electrical conductor which is an electrically insulated wire or cable can be a round cable or wire, i.e. the thickness of the cable or wire in all dimensions is almost the same. Alternatively, the at least one electrical conductor which is an electrically insulated wire or cable is a flat cable or wire, i.e. the thickness of the cable or wire in one dimension is reduced compared to the other dimensions.

Such flat cable or wire may result in a more flexible stretchable electrode assembly at higher conductivity by increased conductor cross section with lower or same height compared to a round cable or wire. Thus, in one embodiment, the at least one electrical conductor which is an electrically insulated wire or cable is a flat cable or wire.

It is preferred in one embodiment that the at least one electrical conductor which is an electrically insulated wire or cable is arranged in a meandering form in the stretchable electrode assembly. Arranging the at least one electrical conductor in such a form has the advantage that the resulting assembly provides a sufficient flexibility and is thus specifically suitable for the products to be prepared.

The at least one electrical conductor is an electrically insulated wire or cable. Accordingly, the at least one electrical conductor comprises a metal wire or cable and an insulation or consists of one or more metal wires or cables and an insulation. In some embodiments, the at least one electrical conductor comprises one or more of the metals Pt, Ir, Ta, Pd, Ti, Fe, Au, Mo, Nb, W, Ni, Ti, Ag, Cu, or a mixture and/or alloy thereof. In some embodiments, the at least one electrical conductor comprises the alloys MP35N, PtIr10, PtIr20, 316L, 301 or nitinol.

In one embodiment, the at least one electrical conductor comprises MP35N, Cu, Au, Ta, Pt, Ir or Pd. In some embodiments, the electrically conductive part of the at least one electrical conductor consists of MP35N, Cu, Au, Ta, Pt, Ir or Pd or alloys of said metals. In some embodiments, the at least one electrical conductor contains less than 3%, 2% or less than 1% Fe. MP35N is a nickel-cobalt-based hardenable alloy. A variant of MP35N is described in the industrial standard ASTM F562-13. In one embodiment, MP35N is an alloy that comprises 33 to 37% Co, 19 to 21% Cr, 9 to 11% Mo, and 33 to 37% Ni. For example, the at least one electrical conductor comprises MP35N/Ag.

PtIr10 is an alloy made of 88 to 92% platinum and 8 to 12% iridium.

PtIr20 is an alloy made of 78 to 82% platinum and 18 to 22% iridium.

316L is an acid-resistant, CrNiMo austenitic steel with approx. 17% Cr; approx. 12% Ni and at least 2.0% Mo. One variant of 316L is described in the industrial standard EN 10088-2. In one embodiment, 316L is an alloy that comprises 16.5 to 18.5% Cr, 2 to 2.5% Mo, and 10 to 13% Ni.

301 is a chromium-nickel steel with high corrosion resistance. One variant of 301 is described in the industrial standard DIN 1.4310. In one embodiment, 301 is an alloy that comprises 16 to 18% Cr and 6 to 8% Ni.

Nitinol is a nickel-titanium alloy with a shape memory with an ordered-cubic crystal structure and a nickel fraction of approximately 55%, whereby titanium accounts for the remaining fraction. Nitinol has good properties with regard to biocompatibility and corrosion resistance. Unless specified otherwise, all percentages given herein shall be understood to be mass percentages (weight %).

It is appreciated that the at least one electrical conductor should have a high electrical conductivity and fatigue resistance. Thus, the at least one electrical conductor in one embodiment comprises a wire or cable being a MP35N wire or cable with Ag core (MP35N/Ag). That is to say, the electrically conductive part of the at least one electrical conductor in one embodiment consists of a MP35N wire or cable with Ag core. The at least one electrical conductor may also comprise multilayered material systems.

It is preferred in one embodiment that the electrically conductive part of the at least one electrical conductor, i.e. the wire or cable, consists of one or more of said materials and an insulation.

The at least one electrical conductor is electrically insulated, in one embodiment by an insulating plastic material. In as far as multiple electrical conductors are present, these comprise no electrical connection to each other. In some embodiments, the at least one electrical conductor comprises a dielectric sheathing, for example made of an electrically insulating plastic material, silicone or rubber. Suitable insulating plastic materials are selected from the group comprising polyethylene, polyurethane, polyimide, polyamide, PEEK, and fluorinated plastic materials such as ETFE, PTFE, PFA, PVDF, FEP or FPO, and mixtures thereof. The insulating plastic material is in one embodiment selected from the group comprising polyurethane, polyimide, and fluorinated plastic material such as ETFE, PTFE, PFA or FEP.

It is preferred in one embodiment that the insulation of the at least one electrical insulation has a thickness ranging from 3 to 150 μm, in one embodiment ranging from 5 to 40 μm.

A plurality of electrical conductors, i.e. either a wire or a cable can be arranged into a conductor bundle. Thus, the at least one electrical conductor of the electrical conductor segment may be in the form of a bundle of electrical conductors, wherein each electrical conductor is electrically insulated. In one embodiment, the conductor bundle of electrical conductors further comprises an electrically insulation encompassing the conductor bundle. Such arrangement has the benefit that more electrodes can be attached to each single cable, whereby all electrode are selectively contacted. This would result in less required cable lines in the final assembly.

It is appreciated that the at least one electrical conductor which is an electrically insulated wire or cable forms an electrical conductor segment in the stretchable electrode assembly. Such conductor bundle in one embodiment comprises from two to ten wires or cables.

The term "segment" in the meaning of the present embodiments refers to a distinct area (or layer) within the stretchable electrode assembly.

It is further to be noted that the electrical insulation of the at least one electrical conductor comprises one or more opening(s) suitable for mechanically and electrically connecting the at least one electrode to the at least one electrical conductor of the electrical conductor segment.

The number of opening(s) in the electrical insulation of the at least one electrical conductor depends on the number of electrodes connected to the at least one electrical conductor.

Thus, the at least one electrical conductor may include one opening in the electrical insulation of the at least one electrical conductor. In this case, only one electrode is connected to the at least one electrical conductor.

Alternatively, the at least one electrical conductor includes two or more openings, e.g. two to ten openings, in the electrical insulation of the at least one electrical conductor. In this case, two or more, e.g. two to ten, electrodes are connected to the at least one electrical conductor.

Thus, it is preferred in one embodiment that the number of openings in the electrical insulation of the at least one electrical conductor corresponds to the number of electrodes connected to the at least one electrical conductor.

If the stretchable electrode assembly comprises more than one electrical conductor, it is appreciated that each electrical conductor may include a different number of opening(s), i.e. also a different number of electrodes. However, it is preferred in one embodiment that each electrical conductor in such an arrangement includes the same number of opening (s).

It is preferred in one embodiment that the material of the electrode surrounds the entire circumference of the opening of the at least one electrical conductor to which the electrode is connected to.

In one embodiment, the opening(s) comprises a varying diameter. For example, the opening(s) can be cone-shaped. In one embodiment, the opening(s) can comprise a smaller diameter on the external side than on the internal side.

In one embodiment, the opening(s) comprise(s) a diameter, at the surface, perpendicular to its longitudinal direction of less than 0.2 mm. In a further embodiment, the diameter of the opening(s) is/are less than 0.1 mm. The diameter of the opening(s) is/are in one embodiment at least 10 μm in size. In one embodiment, the diameter of the opening(s) is/are larger than the diameter of the conductor. In one embodiment, the diameter of the opening(s) is larger than the diameter of the wire in the at least one electrical conductor.

The stretchable electrode assembly for the stimulation, modulation or sensing implant further comprises at least one electrode which is adjacent to the electrical conductor segment.

The term "adjacent" in the meaning of the present embodiments means that the at least one electrode and the electrical conductor segment are in direct contact with each other. Thus, there is no further layer between the at least one electrode and the electrical conductor segment. It is appreciated that the term "adjacent" includes that the at least one electrode is placed only on one side of the electrical conductor segment, i.e. on the top or bottom side of the electrical conductor segment, and in one embodiment of the stretchable electrode assembly. Alternatively, the at least one electrode(s) surround(s) one of the electrical conductor(s) of the electrical conductor segment, in one embodiment if the at least one electrode is a ring electrode.

The electrode is a conductive and electrically conductive element, which can be attached appropriately to the at least one electrical conductor or conductor bundle.

In some embodiments, the at least one electrode comprises one or more of the metals Pt, Ir, Ta, Pd, Ti, Fe, Au, Mo, Nb, W, Ni, Ti, Ag, Cu, or a mixture and/or alloy thereof. It is to be noted that the at least one electrode may be in contact with tissue and thus, it is especially preferred in one embodiment that it is made of a biocompatible material. In view of this, it is preferred in one embodiment that the at least one electrode comprises Au or one of the alloys MP35N, PtIr20, PtIr10, PdIr10, 316L, or 301. The electrode can just as well comprise multilayered material systems. In one embodiment, the electrode consists of one or more of said materials.

In view of the different needs in terms of high electrical conductivity and teak resistance of the at least one electrical conductor on one side and the high biocompatibility of the at least one electrode on the other side, it is preferred in one embodiment that the at least one electrical conductor, i.e. the conductive part of the electrical conductor, and the at least one electrode comprise different materials.

Thus, it is preferred in one embodiment that the electrically conductive part of the at least one electrical conductor in one embodiment consists of a MP35N wire or cable with Ag core (MP35N/Ag), whereas the at least one electrode comprises Au or one of the alloys MP35N, PtIr20, PtIr10, PdIr10, 316L, or 301.

In one embodiment, the at least one electrode has an external diameter of less than 2 mm, in one embodiment in the range from 20 μm to 2 mm and in one embodiment from 100 μm to 1 mm.

Additionally or alternatively, the at least one electrode has a length ranging from 50 μm to 5 mm and in one embodiment from 100 μm to 1 mm.

The type of electrode is not particularly limited as long as the electrode is suitable for use in an implant. For example, the at least one electrode may be a cubic, rectangular, cylindrical or ring electrode or an electrode segment, in one embodiment a flat electrode segment. In one embodiment, the at least one electrode is a ring electrode or an electrode segment, in one embodiment a flat electrode segment.

It is appreciated that the at least one electrode forms an electrode segment in the stretchable electrode assembly.

It is further to be noted that the electrical insulation of the at least one electrical conductor comprises one or more opening(s) suitable for mechanically and electrically connecting the at least one electrode to the at least one electrical conductor of the electrical conductor segment. The mechanical and electrical connection between the at least one electrode and the at least one electrical conductor of the electrical conductor segment can be achieved by any means known to the skilled person resulting in a firmly-bonded connection. For example, the at least one electrode is/are mechanically and electrically connected to the at least one electrical conductor by welding, adhesives, brazing, soldering, conductive polymer or metal bridges, and/or dimples which are pressed, e.g. by crimping or swaging, through the opening of the electrical insulation of the at least one electrical conductor. In case more than one electrode is connected to the at least one electrical conductor of the electrical conductor segment, the connection is in one embodiment the same for all connections present.

The mechanical and electrical connection between the at least one electrode and the at least one electrical conductor is in one embodiment achieved by welding, brazing and/or soldering such as soft soldering. Additionally or alternatively, the mechanical and electrical connection between the at least one electrode and the at least one electrical conductor can be achieved by adhesives and/or dimples which are pressed, e.g. by crimping or swaging, through the opening of the electrical insulation of the at least one electrical conductor.

Additionally or alternatively, the mechanical and electrical connection between the at least one electrode and the at least one electrical conductor can be achieved by conductive polymer or metal bridges through the opening of the electrical insulation of the at least one electrical conductor. In this embodiment, the opening of the electrical insulation of the at least one electrical conductor is filled with a conductive polymer and the electrode, in one embodiment ring electrode, is pressed on to it. The conductive polymer may be applied in form of a paste or by a Galvano chemical process.

In one embodiment, the mechanical and electrical connection between the at least one electrode and the at least one electrical conductor is achieved by only one means, i.e. by welding, adhesives, brazing, soldering, conductive polymer or metal bridges, or dimples which are pressed, e.g. by crimping or swaging, through the opening of the electrical insulation of the at least one electrical conductor.

In one embodiment, the mechanical and electrical connection between the at least one electrode and the at least one electrical conductor in a firmly-bonded manner. In this case, the mechanical and electrical connection between the at least one electrode and the at least one electrical conductor is in one embodiment a welded connection. Said welded connection can be attained, for example, by laser welding. The melting of the conductor in the course of welding can be used to completely close the opening of the electrical insulation of the at least one electrical conductor. By this means, the ingress of liquids or other contaminations into the opening can be prevented. Moreover, sharp edges or burrs on the external side of the opening can be covered and therefore smoothed.

Having an exclusively firmly-bonded connection results in a very stable, durable and very conductive connection between the conductor and the electrode. This is of particular advantage if the electrode comprises a certain surface structure and shall still maintain such structure after the contacting to the conductor. For example, particularly smooth electrode surfaces with a precisely defined geometry can be attained by this means.

In one embodiment, the mechanical and electrical connection between the at least one electrode and the at least one electrical conductor is achieved in a force-locking manner. Said force-locking connection can be achieved by e.g. dimples or other mechanical pressing methods known in this field. Several suitable methods are described in EP3185248A1. Comparable methods known in this context to a person skilled in the art can be used as well.

In one embodiment, the mechanical and electrical connection between the at least one electrode and the at least one electrical conductor is achieved in a direct firmly-bonded manner. In one embodiment, the mechanical and electrical connection between the at least one electrode and the at least one electrical conductor is achieved in a direct force-locking manner. In one embodiment, the mechanical and electrical connection between the at least one electrode and the at least one electrical conductor is achieved in a direct firmly-bonded as well as a direct force-locking manner. In one embodiment, the mechanical and electrical connection between the at least one electrode and the at least one electrical conductor is achieved in a direct firmly-bonded manner, but not in a force-locking manner.

It is to be noted that the at least one electrical conductor is in one embodiment connected to the at least one electrode within the opening in a form-fitting manner.

In one embodiment, the at least one electrical conductor is connected to the at least one electrode in a firmly-bonded manner, but not in a force-locking manner. The at least one electrical conductor can just as well be connected to the at least one electrode exclusively in a firmly-bonded manner.

In one embodiment, the at least one electrode is micro-structured, i.e. it comprises surface structures, or a coated. Said surface structures can impart a higher and precisely defined roughness to the electrode surface. The surface structures can be generated even before connecting the at least one electrode to the at least one electrical conductor as they are not affected by a force-locking connection. It is also possible to micro-structure the at least one electrode after attaching it to the at least one electrical conductor.

Similarly, it is feasible to use coated electrodes. Said coatings are in one embodiment used if the mechanical and electrical connection between the at least one electrode and the at least one electrical conductor of the electrical conductor segment is of an exclusively firmly-bonded manner. Such a coating is not affected by the inventive contacting of the at least one electrical conductor to the at least one electrode.

In one embodiment, the stretchable electrode assembly comprises a multitude of electrodes, wherein each is electrically and mechanically connected to exactly one of the electrical conductors, such that the multitude of electrodes can be electrically addressed independent of each other. This means that each of the multitude of electrodes is set up to receive an electrical signal exclusively from exactly one electrical conductor or to emit an electrical signal to said electrical conductor, but not to any of the other electrical conductors. Accordingly, each electrode can be electrically triggered independent of the other electrodes.

In one embodiment, other than the direct connection between the at least one conductor and the at least one electrode, there is no further component present that connects the at least one electrical conductor to the at least one electrode in order to establish an electrical and mechanical connection between them. According to one embodiment, a welded or soldered connection or a material forming a connection of this type shall not be understood to be a "component" in this context. A component of this type could, e.g., be an adhesive or dimples, which is attached to the wire or cable of the at least one electrical conductor in order to subsequently connect it to the at least one electrode.

It is further required by the present embodiment that the electrical conductor segment is at least partially embedded in a biocompatible substrate. For example, the electrical conductor segment is partially embedded in the biocompatible substrate. Alternatively, the electrical conductor segment is essentially completely embedded in the biocompatible substrate.

In addition to the electrical conductor segment, the stretchable electrode assembly further comprises at least one electrode. In one embodiment, the electrical conductor segment and the at least one electrode are at least partially embedded in the biocompatible substrate. For example, the electrical conductor segment and the at least one electrode are partially embedded in the biocompatible substrate. Alternatively, the electrical conductor segment and the at least one electrode are essentially completely embedded in the biocompatible substrate.

If the electrical conductor segment and the at least one electrode are at least partially embedded in the biocompatible substrate, it is preferred in one embodiment that the electrical conductor segment is at least partially embedded in the biocompatible substrate, whereas the at least one electrode is not in contact with the biocompatible substrate.

However, it is favourable for the stretchability of the stretchable electrode assembly if the electrical conductor segment and the at least one electrode are essentially completely embedded in the biocompatible substrate. Furthermore, the electrical conductor segment and the at least one electrode are protected from mechanical or chemical damages such as from surrounding liquids or tissue.

The biocompatible substrate may be any polymeric material known to be suitable for the products to be prepared.

The term "biocompatible" in the meaning of the present embodiments is meant to refer to a material which is considered by a person skilled in the art to be safe when being in contact with a living organism (e.g. a human) over a specific period of time (e.g. when used in an implantable medical device).

For example, the biocompatible substrate is selected from the group comprising polyurethane, thermoplastic polyurethane (TPU), silicone, polyimide, phenyltrimethoxysilane (PTMS), polymethylmethacrylate (PMMA), parylene, polyetheretherketone (PEEK), liquid-crystal polymer (LCP), kapton and mixtures thereof. In one embodiment, the biocompatible substrate is silicone.

In order to obtain a firm connection between the biocompatible substrate and the electrical conductor segment and optionally the at least one electrode, the components are in one embodiment welded joint. It is appreciated that the biocompatible substrate and the electrical conductor segment and optionally the at least one electrode may be also fusion joint.

In view of the above, a stretchable electrode assembly for a stimulation, modulation or sensing implant as defined herein is provided.

The term "stretchable" in the meaning of the present embodiments refers to an assembly that can be elongated along the x- and y-axes in the xyz-dimensional space, i.e. along the length and width of the stretchable electrode assembly, and will go back to its initial form after removing the external tension.

Furthermore, the stretchable electrode assembly is in one embodiment flexible. It is appreciated that the flexibility of the assembly is achieved by the specific arrangement of the wire(s) or cable(s). For example, the wire(s) or cable(s) is/are in one embodiment arranged in a meandering form.

The term "flexible" in the meaning of the present embodiments refers to an assembly that can be bended in all directions without fractures.

The stretchable electrode assembly has in one embodiment a thickness ranging from 0.4 to 1.5 mm, in one embodiment from 0.4 to 1.2 mm.

In view of the arrangement of the electrical conductor segment and the at least one electrode and embedding these components at least partially, in one embodiment essentially completely, into a biocompatible substrate, the electrode assembly is not only stretchable but also soft. Thus, the electrode assembly is in one embodiment a soft and stretchable electrode assembly.

The term "soft" in the meaning of the present embodiments refers to a device that is yielding to pressure, in one embodiment without breaking up the device. It is appreciated that the softness is desired as it helps to attach the assembly to a given structure inside the body and the assembly shape will match to the structure inside the body.

Thus, the stretchable electrode assembly is particularly suitable for a stimulation, modulation or sensing implant. It is appreciated that the stretchable electrode assembly in one embodiment forms the distal part of the implant. Additionally, the implant in one embodiment further includes a connector which is assembled to the proximal wire ends.

In a further aspect, the present embodiment thus relates to a stimulation, modulation or sensing implant comprising the stretchable electrode assembly as defined herein. According to one embodiment, the stimulation, modulation or sensing implant is in one embodiment a neuro modulation device, spinal cord stimulator, neuro stimulator device, cortical mapping device, heart muscle stimulator device or electrophysiology device. Particularly, the stimulation, modulation or sensing implant is a neuro modulation device, spinal cord stimulator, neuro stimulator device or cortical mapping device.

According to another aspect of the present embodiment, a method for preparing a stretchable electrode assembly as defined herein is provided. The method comprises the steps of a) providing at least one electrical conductor which is an electrically insulated wire or cable,
b) providing at least one electrode,
c) providing a biocompatible substrate,
d) adding one or more opening(s) into the electrical insulation of the at least one electrical conductor suitable for mechanically and electrically connecting the at least one electrode to the at least one electrical conductor,
e) assembling the at least one electrode to the one or more opening(s) in the electrical insulation of the at least one electrical conductor, whereby a mechanical and electrical connection between them is formed in a firmly-bonded and/or force-locked manner, and
f) covering the at least one electrical conductor before or after step d) and/or before or after step e) with the biocompatible substrate such that the electrical conductor is at least partially embedded in the biocompatible substrate.

As regards the at least one electrical conductor, the at least one electrode, the biocompatible substrate and preferred embodiments thereof, it is referred to the comments provided above when discussing the stretchable electrode assembly in more detail.

According to step d) of the present method, one or more opening(s) suitable for mechanically and electrically connecting the at least one electrode is/are added into the electrical insulation of to the at least one electrical conductor.

It is appreciated that the one or more opening(s) suitable for mechanically and electrically connecting the at least one electrode to the at least one electrical conductor is/are added into the electrical insulation of the at least one electrical conductor where the at least one electrode is to be connected to the at least one electrical conductor.

In principle, the one or more opening(s) can be obtained by any known method, which is capable of forming one or more opening(s) in the electrical insulation of the at least one electrical conductor.

Laser ablation is particularly suitable to form the one or more opening(s) in the electrical insulation of the at least one electrical conductor. Thus, according to one embodiment, the one or more opening(s) in the electrical insulation of the at least one electrical conductor is/are obtained by laser ablation.

Laser ablation relates to a process of removing material from a solid surface by irradiating the surface with a laser beam. The material of the irradiated surface evaporates, sublimates, and/or is converted to a plasma. The laser ablation step may be carried out using a galvanometer scanner and/or a x-, y-, z- and rotation-axis for the positioning the laser on the surface of the monolithic substrate or the electrode, respectively. Laser ablation and the equipment therefor are known to the skilled person.

According to one embodiment, the laser ablating step b) is carried out with a pulsed laser, more in one embodiment with an ultrashort pulsed laser. Alternatively, the laser ablating step b) is carried out with a nanosecond laser.

According to one embodiment, the laser ablating is carried out with a laser pulse repetition rate of 50 to 500 kHz, and in one embodiment in the range of 100 to 200 kHz, and/or a laser pulse duration of 100 fs to 10 ns, and in one embodiment in the range of 500 fs to 1500 ps, and/or a laser pulse energy in the range of 100 nJ to 100 μJ, and in one embodiment 500 nJ to 20 μJ.

According to one embodiment, the laser ablating is carried out with a laser pulse repetition rate of 50 to 500 kHz, and in one embodiment in the range of 100 to 200 kHz, and a laser pulse duration of 100 fs to 10 ns, and in one embodiment in the range of 500 fs to 1500 ps, and a laser pulse energy in the range of 100 nJ to 100 μJ, and in one embodiment 500 nJ to 20 μJ.

According to step e) of the method, the at least one electrode is assembled to the one or more opening(s) of the at least one electrical conductor, whereby a mechanical and electrical connection between them is formed in a firmly-bonded and/or force-locked manner. In one embodiment, the at least one electrode is assembled to the one or more opening(s) of the at least one electrical conductor, whereby a mechanical and electrical connection between them is formed in a firmly-bonded manner.

As already described in detail above, the at least one electrode is/are mechanically and electrically connected to the at least one electrical conductor by welding, adhesives, brazing, soldering, conductive polymer or metal bridges, and/or dimples which are pressed through the opening of the electrical insulation of the at least one electrical conductor. In one embodiment, the at least one electrode is/are mechanically and electrically connected to the at least one electrical conductor by welding.

Such methods are well known to the skilled person.

According to step f) of the method, the at least one electrical conductor is covered before or after step d) or before or after step e) with the biocompatible substrate such that the electrical conductor is at least partially embedded in the biocompatible substrate.

It is appreciated that the biocompatible substrate may be added on the electrical conductor by any means known in the art. For example, the at least one electrical conductor is covered before or after step d) or before or after step e) with the biocompatible substrate in form of a foil. Alternatively, the at least one electrical conductor is covered before or after step d) or before or after step e) with the biocompatible substrate by molding, spin coating or CVD.

In one embodiment, the at least one electrical conductor is covered before or after step d) or before or after step e) with the biocompatible substrate such that the electrical conductor is at essentially completely embedded in the biocompatible substrate.

It is preferred in one embodiment that the at least one electrical conductor is covered before or after step d) or before or after step e) and welded joint or fusion joint, in one embodiment welded joint, with the biocompatible substrate. Alternatively, the at least one electrical conductor is covered before or after step d) or before or after step e) and molded, spin coated, hot pressed (or laminated) or treated by CVD with the biocompatible substrate.

Such methods are well known to the skilled person.

In one embodiment, the at least one electrical conductor is covered after step d) and after step e) with the biocompatible substrate such that the electrical conductor is at least partially embedded in the biocompatible substrate. In this embodiment, the electrical conductor and the at least one electrode are in one embodiment essentially completely embedded in the biocompatible substrate.

Thus, the method in one embodiment comprises the steps of a) providing at least one electrical conductor which is an electrically insulated wire or cable,
b) providing at least one electrode,
c) providing a biocompatible substrate,
d) adding one or more opening(s) into the electrical insulation of the at least one electrical conductor suitable for mechanically and electrically connecting the at least one electrode to the at least one electrical conductor,
e) assembling the at least one electrode to the one or more opening(s) in the electrical insulation of the at least one electrical conductor, whereby a mechanical and electrical connection between them is formed in a firmly-bonded and/or force-locked manner, and
f) covering the at least one electrical conductor after step d) and/or after step e), in one embodiment after step e) with the biocompatible substrate such that the electrical conductor and optionally the at least one electrode is/are at least partially, in one embodiment essentially completely, embedded in the biocompatible substrate.

It is preferred in one embodiment that the assembly of step e) is arranged in one or more pre-shaped groove(s) of fixture before step f) is carried out. In one embodiment, the assembly is arranged in a meandering form. In this embodiment, the assembly of step e) is in one embodiment covered with the biocompatible substrate such that the assembly is partially embedded in the biocompatible substrate. Furthermore, the assembly which is partially embedded in the biocompatible substrate can be removed from the pre-shaped groove(s) of fixture, turned around and essentially completely covered with the biocompatible substrate. In one embodiment, the at least one electrical conductor is covered before step d) and before step e) with the biocompatible substrate such that the electrical conductor is at least partially embedded in the biocompatible substrate.

Thus, the method in one embodiment comprises the steps of:

a) arranging the at least one electrical conductor in one or more pre-shaped groove(s) of fixture to form an electrical conductor segment,
b) covering the electrical conductor segment with the biocompatible substrate such that the electrical conductor segment is partially embedded in the biocompatible substrate,
c) removing the electrical conductor segment which is partially embedded in the biocompatible substrate from the pre-shaped groove(s) of fixture,
d) adding one or more opening(s) into the electrical insulation of the at least one electrical conductor suitable for mechanically and electrically connecting at least one electrode to the at least one electrical conductor, and
e) assembling at least one electrode to the one or more opening(s) in the electrical insulation of the at least one electrical conductor, whereby a mechanical and electrical connection between them is formed in a firmly-bonded and/or force-locked manner.

According to one aspect, a method for preparing a stretchable electrode assembly as defined herein is thus provided, the method comprising the steps of:

a) arranging the at least one electrical conductor in one or more pre-shaped groove(s) of fixture to form an electrical conductor segment,
b) covering the electrical conductor segment with the biocompatible substrate such that the electrical conductor segment is partially embedded in the biocompatible substrate,
c) removing the electrical conductor segment which is partially embedded in the biocompatible substrate from the pre-shaped groove(s) of fixture,
d) adding one or more opening(s) into the electrical insulation of the at least one electrical conductor suitable for mechanically and electrically connecting at least one electrode to the at least one electrical conductor, and
e) assembling at least one electrode to the one or more opening(s) in the electrical insulation of the at least one electrical conductor, whereby a mechanical and electrical connection between them is formed in a firmly-bonded and/or force-locked manner.

It is appreciated that the steps described above and in the following for the corresponding methods apply to each method described herein accordingly.

According to step a), the at least one electrical conductor is arranged in one or more pre-shaped groove(s) of fixture, depending on the number of electrical conductors, to form an electrical conductor segment. Thus, the number of pre-shaped groove(s) of fixture typically corresponds to the number of electrical conductors.

It is preferred in one embodiment that the one or more pre-shaped groove(s) of fixture provide the final shape of the stretchable electrode assembly. In one embodiment, the one or more pre-shaped groove(s) of fixture provide the arrangement and form of the at least one electrical conductor and optionally of the stretchable electrode assembly. It is also possible that the stretchable electrode assembly is shaped and formed after the method has been carried out to bring the assembly into the final shape.

It is to be noted that the pre-shaped groove(s) of fixture may provide any form or shape, i.e. regular or irregular, that may be desired for the stretchable electrode assembly. Additionally or alternatively, if the stretchable electrode assembly comprises two or more electrical conductors, the pre-shaped grooves of fixture can be parallel to each other, or they can be arranged independently of each other. As a result, the electrical conductors in the obtained stretchable electrode assembly are parallel to each other, or they are arranged independently of each other. In one embodiment, the at least one electrical conductor is arranged in a meandering form in the stretchable electrode assembly. Arranging the at least one electrical conductor in such a form has the advantage that the resulting assembly provides a sufficient flexibility and is thus specifically suitable for the products to be prepared.

In order to assembly the at least one electrode to the at least one electrical conductor of the electrical conductor segment, it is preferred in one embodiment that the electrical conductor segment is partially embedded in the biocompatible substrate such that at least one electrode can be assembled to the at least one electrical conductor opposite the biocompatible substrate, i.e. the part of the at least one electrical conductor which is not embedded in the biocompatible substrate. Thus, step b) of the method in one embodiment comprises covering the electrical conductor segment with the biocompatible substrate such that the electrical conductor segment is partially embedded in the biocompatible substrate.

In view of this, step c) of the method comprises the removal of the electrical conductor segment which is partially embedded in the biocompatible substrate from the pre-shaped groove(s) of fixture. As the one or more opening(s) suitable for mechanically and electrically connecting at least one electrode are in one embodiment added to the at least one electrical conductor opposite the biocompatible substrate, the at least one electrical conductor segment which is partially embedded in the biocompatible substrate is removed from the pre-shaped groove(s) of fixture and in one embodiment turned around.

As already mentioned above, the at least one electrode may be micro-structured or coated. In one embodiment, the method of the present embodiment may thus comprise a further step of micro-structuring or coating the at least one electrode of the stretchable electrode assembly. In general, this step can be carried out after the step of assembling the at least one electrode to the one or more opening(s) of the at least one electrical conductor. However, it is also possible that the at least one electrode provided in the method is already micro-structured or coated.

The at least one electrode can be structured, for example, by means of a laser. In one embodiment, the surface of the at least one electrode is enlarged by roughening the surface. This can take place with a variety of methods, for example by means of a laser.

A coating can be affected, for example, by means of PVD, CVD or electrochemical deposition, which methods are well known to the skilled person. TiN, Ir, $IrO_x$, Pt or conductive polymers, for example conductive polymers based on thiophene, such as, for example, poly-3,4-ethylenedioxythiophene (PEDOT) or the conductive polymers described in WO/2015/031265, can be used for said coating.

In one embodiment, the electrical conductor segment as well as the at least one electrode are essentially completely embedded in the biocompatible substrate. In this case, the method comprises a further step of covering the at least one electrode of the assembly of step e) with a biocompatible substrate. Thus, the stretchable electrode assembly may comprise a bottom and top layer of the biocompatible substrate. It is appreciated that the bottom and top layer may comprise the same or different biocompatible substrate. It may be advantageous to provide the bottom and top layer with different biocompatible substrates in order to modify the flexibility of the stretchable electrode assembly. However, the bottom and top layer in one embodiment comprise the same biocompatible substrate.

If the electrical conductor segment as well as the at least one electrode are essentially completely embedded in the biocompatible substrate, it may be favourable to further improve the function of the at least one electrode by modifying the surface of same. For this, the biocompatible substrate is in one embodiment ablated, in one embodiment laser ablated, in order to open the electrode surface.

Thus, the method may comprise a further step of (laser) ablating the biocompatible substrate in order to open the electrode surface. The open electrode surface may than be further modified e.g. by a coating with a biocompatible, durable conductive coating, which may optimize the interface between human tissue and the at least one electrode to lower impedance, increase signal fidelity, increase charge injection capacity, lower power requirements and reduce stimulation threshold. Such coatings are for example known as Amplicoat® coating.

It is also possible to attach anchors for spacer in order to keep the stretchable electrode assembly in position once attached to e.g. the target nerve or heart. Thus, the method may comprise a further step of attaching one or more anchors for spacer. Methods for attaching the anchor(s) and materials for said anchor(s) are well known to the skilled person. However, in order to obtain a firm connection between the stretchable electrode assembly, i.e. the biocompatible substrate, and the one or more anchors, the components are in one embodiment welded joint.

The features disclosed in the claims, the specification, and the drawings maybe essential for different embodiments of the claimed invention, both separately and in any combination with each other.

EXAMPLES

The invention is illustrated further in the following based on examples, though these may not be construed such as to limit the invention in any way or form. It will be obvious to a person skilled in the art that, in place of the features described herein, other equivalent means can be used in a similar manner.

The FIGS. 1 to 5 show a schematical illustration of a method suitable for preparing the inventive stretchable electrode assembly.

FIG. 1 shows step 1 of the method in a top and cross-sectional view, wherein pre-shaped groove(s) of fixture are provided in which the at least one electrical conductor can be arranged. The pre-shaped groove(s) of fixture may provide any form or shape, i.e. regular or irregular, that may be desired for the stretchable electrode assembly. According to FIG. 1, multiple pre-shaped grooves of fixture are provided which are parallel to each other in which the electrical conductors are arranged resulting in the parallel arrangement of the electrical conductors. In one embodiment, the electrical conductors are arranged in a meandering form. However, the pre-shaped grooves of fixture can be also arranged independently of each other. It is appreciated that the arrangement of the electrical conductor(s) in the pre-shaped groove(s) of fixture results in the formation of an electrical conductor segment.

Figure 2:
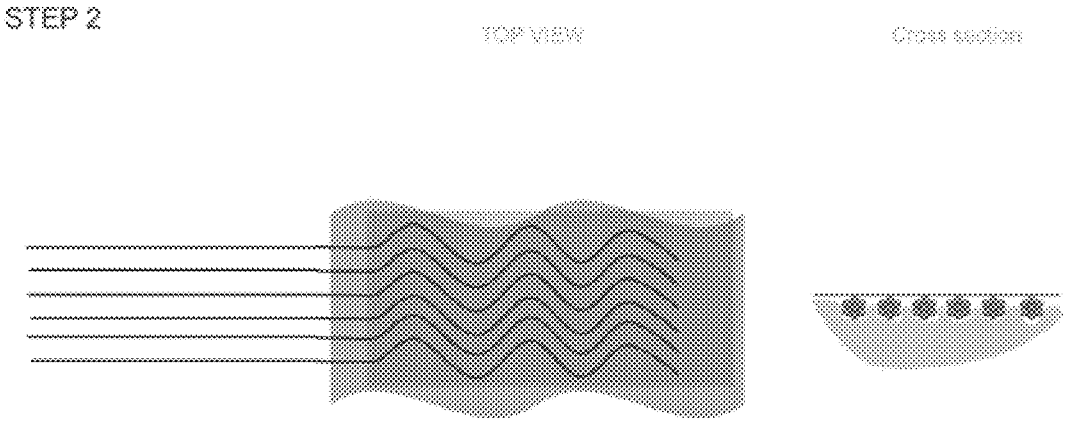
FIG. 2 shows a schematical top and sectional illustration of step 2 of a method for preparing the stretchable electrode assembly.

FIG. 2 shows step 2 of the method in a top and cross-sectional view, wherein the electrical conductor segment is covered with a biocompatible substrate such that the electrical conductor segment is partially embedded in the biocompatible substrate. In this step, the biocompatible substrate forms a top or bottom layer of the biocompatible substrate. The biocompatible substrate is in one embodiment silicone. The biocompatible substrate is in one embodiment added on the electrical conductor segment by using a foil, such as a silicone foil. The electrical conductor segment and the biocompatible substrate are in one embodiment welded joint such that a firmly-bonded connection is achieved between the electrical conductor segment and the biocompatible substrate.

Figure 3:
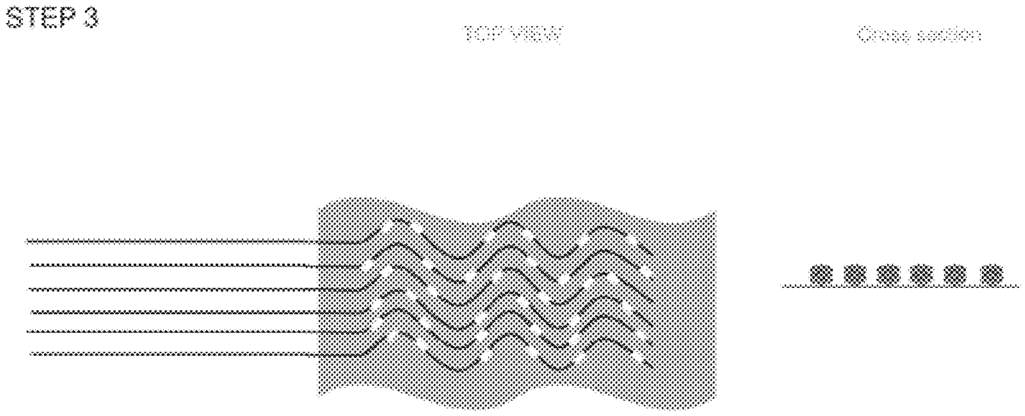
FIG. 3 shows a schematical top and sectional illustration of step 3 of a method for preparing the stretchable electrode assembly.

FIG. 3 shows step 3 of the method in a top and cross-sectional view, wherein the electrical conductor segment which is partially embedded in the biocompatible substrate is removed from the pre-shaped groove(s) of fixture. The one or more opening(s) in the electrical insulation of the at least one electrical conductor is/are in one embodiment added to the at least one electrical conductor opposite the biocompatible substrate. In view of this, the at least one electrical conductor segment which is partially embedded in the biocompatible substrate is removed from the pre-shaped groove(s) of fixture and turned around. Furthermore, one or more opening(s) suitable for mechanically and electrically connecting the at least one electrode to the at least one electrical conductor is/are added into the electrical insulation of the at least one electrical conductor. The one or more opening(s) in the electrical insulation of the at least one electrical conductor is/are in one embodiment obtained by laser ablation.

Figure 4:
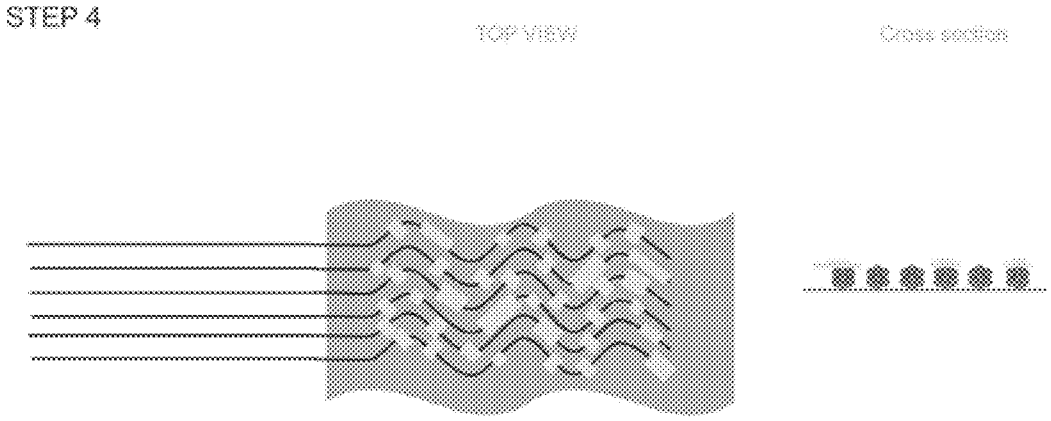
FIG. 4 shows a schematical top and sectional illustration of step 4 of a method for preparing the stretchable electrode assembly.

FIG. 4 shows step 4 of the method in a top and cross-sectional view, wherein at least one electrode is assembled to the one or more opening(s) in the electrical insulation of the at least one electrical conductor, whereby a mechanical and electrical connection between them is formed in a firmly-bonded and/or force-locked manner. It is preferred in one embodiment that the at least one electrode is assembled to the one or more opening(s) in the electrical insulation of the at least one electrical conductor in a firmly-bonded manner. Such a mechanical and electrical connection is in one embodiment obtained by welding.

It is appreciated that the at least one electrode may be micro-structured or coated, which is in one embodiment carried after assembling the at least one electrode to the one or more opening(s) in the electrical insulation of the at least one electrical conductor.

Figure 5:
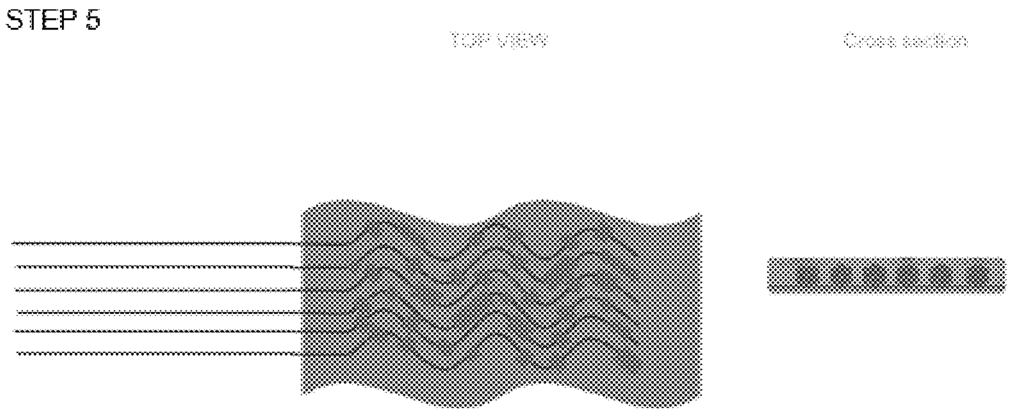
FIG. 5 shows a schematical top and sectional illustration of step 5 of a method for preparing the stretchable electrode assembly.

FIG. 5 shows an optional step 5 of the method in a top and cross-sectional view, wherein the at least one electrode and the electrical conductor segment are essentially completely covered with a biocompatible substrate such that a bottom and top layer is formed. The biocompatible substrate of the bottom and top layers may be the same or different. In one embodiment, the biocompatible substrate of the bottom and top layers is the same. The biocompatible substrate is in one embodiment added on the at least one electrode by using a foil, such as a silicone foil. The at least one electrode (and the electrical conductor segment) and the biocompatible substrate are in one embodiment welded joint such that a firmly-bonded connection is achieved between the at least one electrode (and the electrical conductor segment) and the biocompatible substrate.

The method may comprise a further step of laser ablating the biocompatible substrate in order to open the electrode surface, the open electrode surface may than be further modified by a coating with a biocompatible, durable conductive coating, which may optimize the function of the stretchable electrode assembly.

The method may comprise a further step of attaching one or more anchors for spacer, which may be attached for keeping the stretchable electrode assembly in position once attached to e.g. the target nerve or heart. In order to obtain a firm connection between the stretchable electrode assembly, i.e. the biocompatible substrate, and the one or more anchors, the components are in one embodiment welded joint.

The FIGS. 6 to 10 show a schematical illustration of another method suitable for preparing the inventive stretchable electrode assembly.

Figure 6:
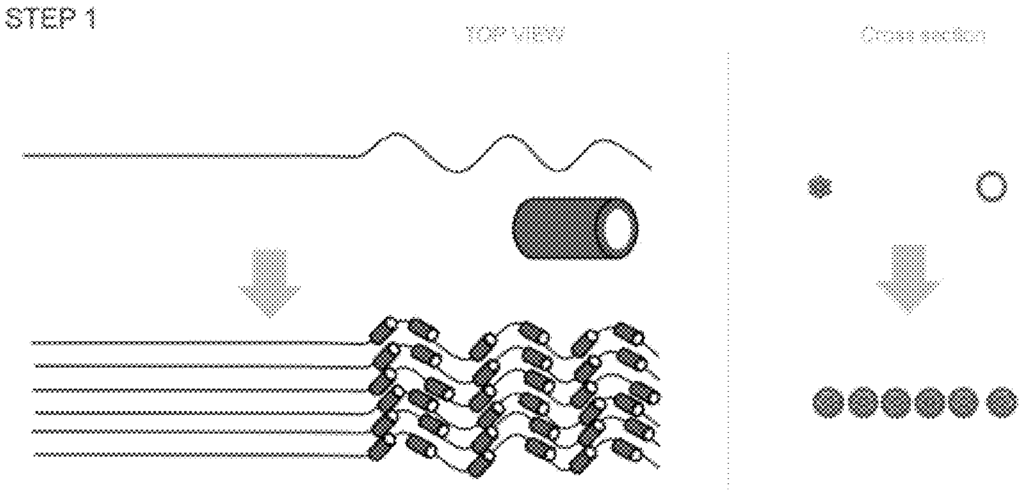
FIG. 6 shows a schematical top and sectional illustration of step 1 of a method for preparing the stretchable electrode assembly.
Figure 7:
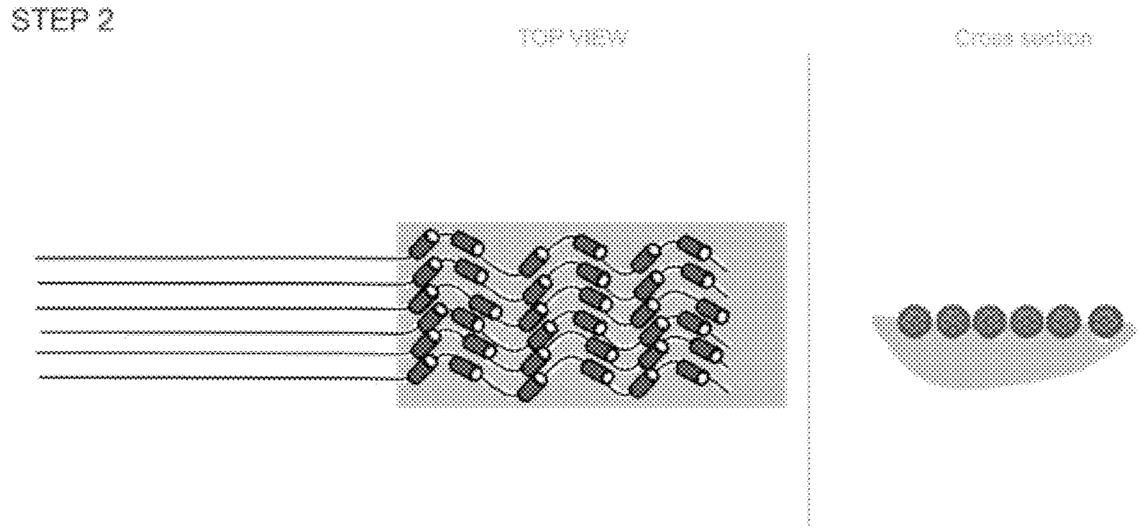
FIG. 7 shows a schematical top and sectional illustration of step 2 of a method for preparing the stretchable electrode assembly.

FIG. 6 shows step 1 of the method in a top and cross-sectional view, wherein at least one electrode, in one embodiment ring electrode(s), is/are assembled to one or more opening(s) in the electrical insulation of the at least one electrical conductor. It is preferred in one embodiment that the at least one electrode is assembled to the one or more opening(s) in the electrical insulation of the at least one electrical conductor in a firmly-bonded manner. Such a mechanical and electrical connection is in one embodiment obtained by welding FIG. 7 shows step 2 of the method in a top and cross-sectional view, wherein pre-shaped groove(s) of fixture are provided in which the assembly of the at least one electrical conductor and at least one electrode can be arranged. The pre-shaped groove(s) of fixture may provide any form or shape, i.e. regular or irregular, that may be desired for the stretchable electrode assembly. According to FIG. 7, multiple pre-shaped grooves of fixture are provided which are parallel to each other in which multiple assemblies of the at least one electrical conductor and at least one electrode are arranged resulting in the parallel arrangement of the assemblies. In one embodiment, the assemblies are arranged in a meandering form. However, the pre-shaped grooves of fixture can be also arranged independently of each other.

Figure 8:
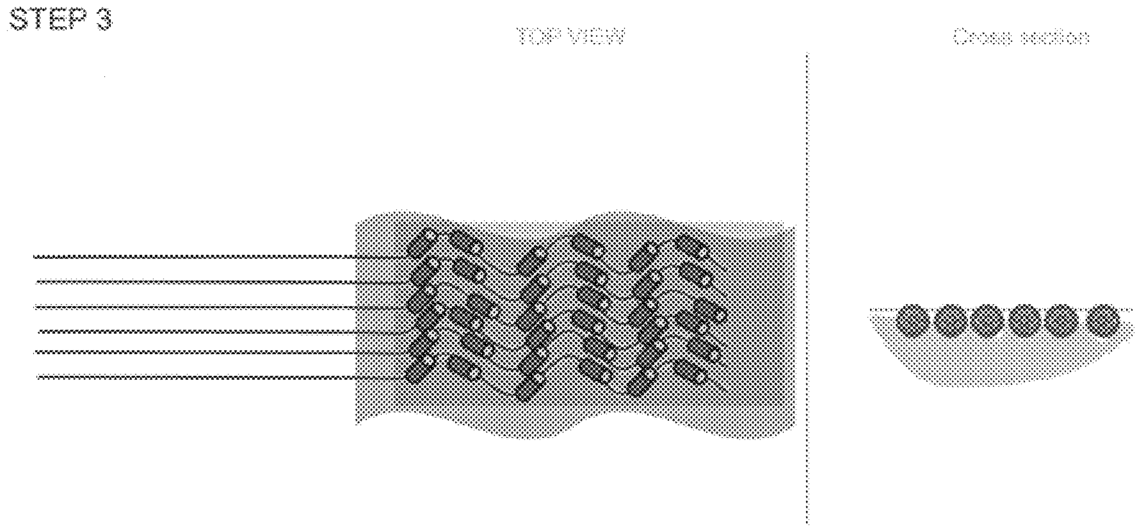
FIG. 8 shows a schematical top and sectional illustration of step 3 of a method for preparing the stretchable electrode assembly.

FIG. 8 shows step 3 of the method in a top and cross-sectional view, wherein the assembly is covered with a biocompatible substrate such that the assembly of the at least one electrical conductor and at least one electrode is partially embedded in the biocompatible substrate. In this step, the biocompatible substrate forms a top or bottom layer of the biocompatible substrate. The biocompatible substrate is in one embodiment silicone. The biocompatible substrate is in one embodiment added on the assembly by using a foil, such as a silicone foil. The assembly and the biocompatible substrate are in one embodiment welded joint such that a firmly-bonded connection is achieved between the assembly and the biocompatible substrate.

Figure 9:
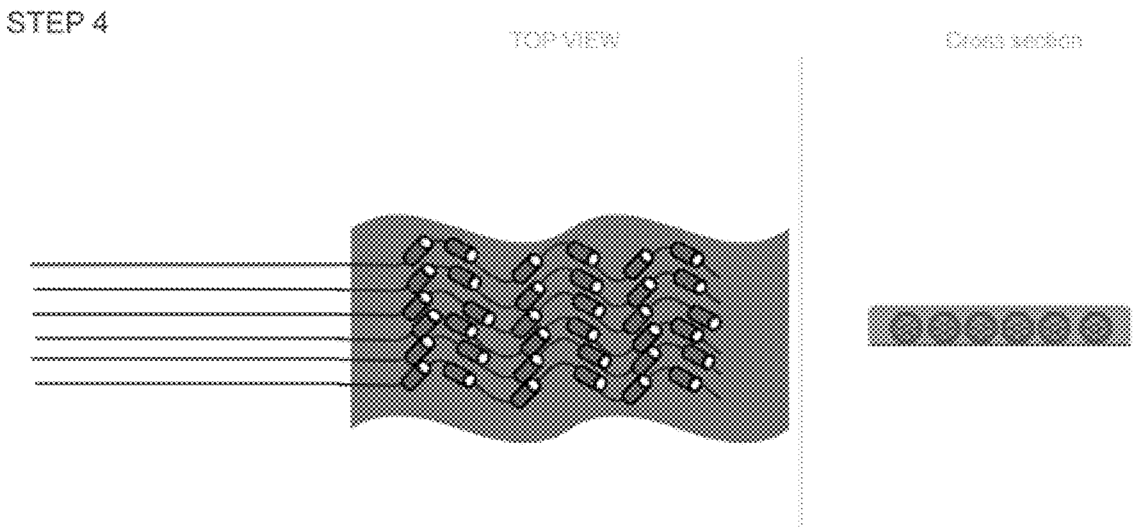
FIG. 9 shows a schematical top and sectional illustration of step 4 of a method for preparing the stretchable electrode assembly.
Figure 10:
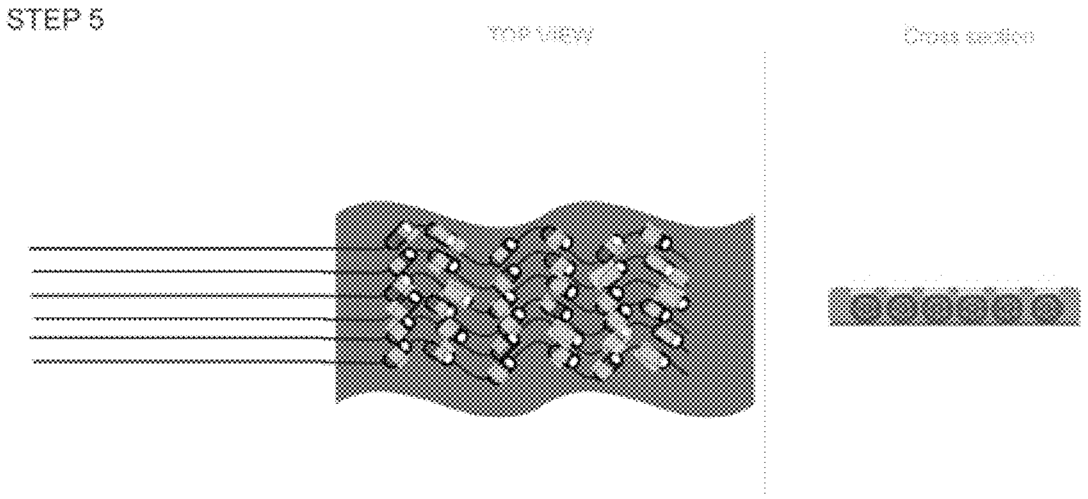
FIG. 10 shows a schematical top and sectional illustration of a further step of laser ablating the biocompatible substrate in order to open the electrode surface.

FIG. 9 shows step 4 of the method in a top and cross-sectional view, wherein the assembly is essentially completely covered with a biocompatible substrate such that a bottom and top layer is formed. In this step, the assembly (assemblies) which is/are partially embedded in the biocompatible substrate is/are removed from the pre-shaped groove (s) of fixture, turned around and then essentially completely covered with the biocompatible substrate. The biocompatible substrate of the bottom and top layers may be the same or different. In one embodiment, the biocompatible substrate of the bottom and top layers is the same. The biocompatible substrate is in one embodiment added on the assembly by using molding, such as a silicone molding. The assembly and the biocompatible substrate are in one embodiment welded joint such that a firmly-bonded connection is achieved between assembly and the biocompatible substrate.

Figure 11:
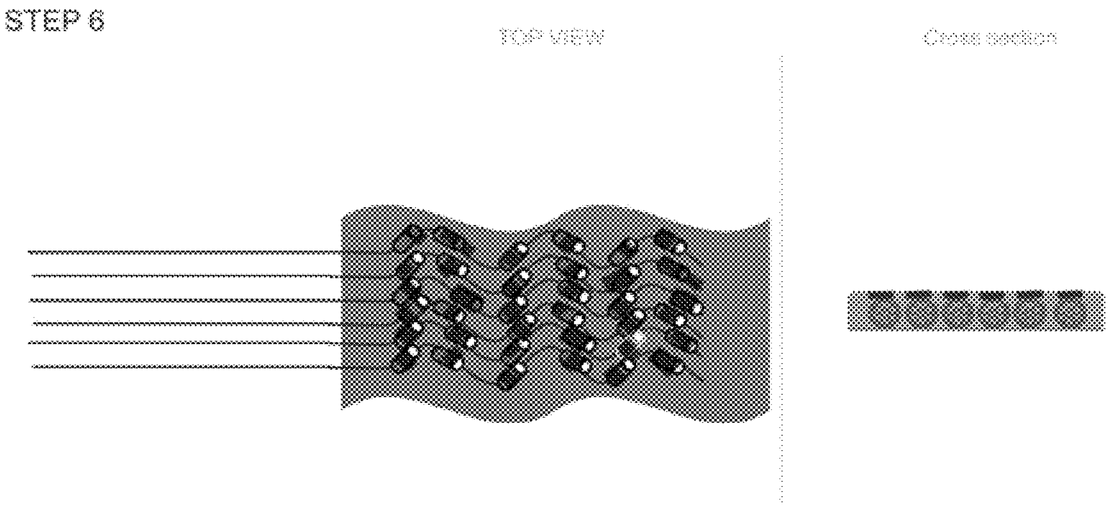
FIG. 11 shows a schematical top and sectional illustration of a further step of modifying the open electrode surface by coating with a biocompatible, durable conductive coating.

The method may comprise a further step of laser ablating (FIG. 10) the biocompatible substrate in order to open the electrode surface, the open electrode surface may than be further modified by a coating with a biocompatible, durable conductive coating, which may optimize the function of the stretchable electrode assembly (FIG. 11).

The method may comprise a further step of attaching one or more anchors for spacer, which may be attached for keeping the stretchable electrode assembly in position once attached to e.g. the target nerve or heart. In order to obtain a firm connection between the stretchable electrode assembly, i.e. the biocompatible substrate, and the one or more anchors, the components are in one embodiment welded joint.

The invention claimed is:

1. A stretchable electrode assembly for a stimulation, modulation or sensing implant comprising an electrical conductor segment comprising two or more electrical conductors, wherein each of the two or more electrical conductors comprise an electrical insulation such that each of the two or more electrical conductors is an individually electrically insulated wire or cable, and at least one electrode which is adjacent to each of the two or more electrical conductors, wherein the electrical conductor segment is at least partially embedded in a biocompatible substrate and the electrical insulation of at least one of the two or more electrical conductors comprises one or more opening(s) configured to mechanically and electrically connect the at least one electrode to at least one electrical conductor of the electrical conductor segment; wherein the stretchable electrode assembly is planar, wherein the two or more electrical conductors are arranged in parallel in the planar shaped stretchable electrode assembly, and wherein the at least one electrode is welded directly to one of the two or more electrical conductors thereby directly coupling, mechanically and electrically, the at least one electrode and one of the two or more electrical conductors and wherein the at least one electrode is a ring electrode surrounding one of the electrical conductors of the electrical conductor segment.

2. The stretchable electrode assembly according to claim 1, wherein the two or more electrical conductors and/or at least one electrode comprise(s) one or more of the metals Pt, I, Ta, Pd, Ti, Fe, Au, Mo, Nb, W, Ni, Ti, Ag, Cu, or a mixture and/or alloy thereof and/or the two or more electrical conductors and/or the at least one electrode is/are a multi-layered material system(s).

3. The stretchable electrode assembly according to claim 1, wherein the electrical insulation of the two or more electrical conductors comprises an insulating plastic material selected from the group consisting of polyethylene, polyurethane, polyimide, polyamide, PEEK, and fluorinated plastic materials.

4. The stretchable electrode assembly according to claim 3, wherein the electrical insulation of the two or more electrical conductors comprises an insulating plastic material selected from the group consisting of ETFE, PTFE, PFA, PVDF, FEP, FPO, and mixtures thereof.

5. The stretchable electrode assembly according to claim 1, wherein the biocompatible substrate is selected from the group consisting of polyurethane, thermoplastic polyurethane (TPU), silicone, polyimide, phenyltrimethoxysilane (PTMS), polymethylmethacrylate (PMMA), parylene, polyetheretherketone (PEEK), liquid-crystal polymer (LCP), and mixtures thereof.

6. The stretchable electrode assembly according to claim 1, wherein the two or more electrical conductors of the electrical conductor segment is a bundle of electrical conductors and each electrical conductor is electrically insulated.

7. The stretchable electrode assembly according to claim 1, wherein the electrical conductor segment and the biocompatible substrate comprise a welded joint.

8. The stretchable electrode assembly according to claim 1, wherein the stretchable electrode assembly has a thickness between 0.4 to 1.5 mm.

9. A stimulation, modulation or sensing implant comprising a stretchable electrode assembly according to claim 1.

10. The stimulation, modulation or sensing implant according to claim 9 that is a neuro modulation device, spinal cord stimulator, neuro stimulator device, cortical mapping device, heart muscle stimulator device or electrophysiology device.

* * * * *